US006712827B2

(12) United States Patent
Ellis et al.

(10) Patent No.: US 6,712,827 B2
(45) Date of Patent: *Mar. 30, 2004

(54) STENT DELIVERY SYSTEM

(75) Inventors: Louis G. Ellis, St. Anthony, MN (US); Andrew J. Dusbabek, Dayton, MN (US); Christopher R. Larson, St. Paul, MN (US); Terry V. Brown, Fridley, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 13 days.

This patent is subject to a terminal disclaimer.

(21) Appl. No.: 10/124,111

(22) Filed: Apr. 16, 2002

(65) Prior Publication Data

US 2002/0123794 A1 Sep. 5, 2002

Related U.S. Application Data

(63) Continuation of application No. 09/420,249, filed on Oct. 19, 1999, now Pat. No. 6,371,962, which is a continuation of application No. 08/702,150, filed on Aug. 23, 1996, now Pat. No. 6,007,543.

(51) Int. Cl.$^7$ ................................................ A61F 11/00
(52) U.S. Cl. ........................ 606/108; 606/195; 606/198; 604/96
(58) Field of Search ................................ 606/108, 195, 606/198; 604/96

(56) References Cited

U.S. PATENT DOCUMENTS

| 4,328,056 A | 5/1982 | Snooks |
| 4,338,942 A | 7/1982 | Fogarty |
| 4,423,725 A | 1/1984 | Baran et al. |
| 4,608,984 A | 9/1986 | Fogarty |
| 4,733,665 A | 3/1988 | Palmaz |
| 4,740,207 A | 4/1988 | Kreamer |
| 4,744,366 A | 5/1988 | Jang |
| 4,848,343 A | 7/1989 | Walsten et al. |

(List continued on next page.)

FOREIGN PATENT DOCUMENTS

| EP | 0 266 957 A2 | 5/1988 |
| EP | 0 442 657 A2 | 9/1991 |
| EP | 0 257 091 B1 | 7/1993 |
| EP | 0 553 960 A1 | 8/1993 |
| EP | 0 627 201 A1 | 12/1994 |

(List continued on next page.)

OTHER PUBLICATIONS

Julio C. Palmaz et al., *Expandable Intraiuminal Graft: A Preliminary Study, Work in Progress*, From the Departments of Radiology (J.C.P., R.R.S., S.R.R.) and Pathology (F.O.T.) University of Texas Health Science Center at Sanantonio and Memorial Medical Center (W.J.K.), Corpus Christi, Texas, *Radiology*, vol. 356, No. 1, pp. 73–77.

*Primary Examiner*—Nicholas D. Lucchesi
*Assistant Examiner*—L Amerson
(74) *Attorney, Agent, or Firm*—Vidas, Arrett & Steinkraus PA

(57) ABSTRACT

A stent delivery system to facilitate introduction and placement of a stent, including a catheter having an expandable distal portion constructed and arranged for expanding the outer diameter of the catheter from a contracted state to an expanded state: a stent positioned around the distal portion of the catheter having a contracted condition and being expandable to an expanded condition, and being sized in the contracted condition to closely surround the catheter in the contracted state, the expandable distal portion of the catheter including a balloon within which there is included on the catheter shaft at least one body of a diameter larger than the catheter shaft to which the stent and balloon are fitted, as by crimping, for holding the stent in place until it is released therefrom by expansion of the balloon.

20 Claims, 4 Drawing Sheets

U.S. PATENT DOCUMENTS

| | | | |
|---|---|---|---|
| 4,875,480 A | | 10/1989 | Imbert |
| 4,950,227 A | * | 8/1990 | Savin et al. ............... 606/192 |
| 5,007,926 A | | 4/1991 | Derbyshire |
| 5,026,377 A | | 6/1991 | Burton et al. |
| 5,037,392 A | | 8/1991 | Hillstead |
| 5,049,132 A | | 9/1991 | Shaffer et al. |
| 5,108,416 A | * | 4/1992 | Ryan et al. ............... 606/194 |
| 5,116,318 A | | 5/1992 | Hillstead |
| 5,158,548 A | | 10/1992 | Lau et al. |
| 5,226,880 A | | 7/1993 | Martin |
| 5,226,889 A | | 7/1993 | Sheiban |
| 5,242,399 A | | 9/1993 | Lau et al. |
| 5,290,306 A | | 3/1994 | Trotta et al. |
| 5,304,198 A | * | 4/1994 | Samson ................... 606/194 |
| 5,342,305 A | | 8/1994 | Shonk |
| 5,344,402 A | | 9/1994 | Crocker |
| 5,344,426 A | | 9/1994 | Lau et al. |
| 5,358,487 A | | 10/1994 | Miller |
| 5,378,237 A | | 1/1995 | Boussignac et al. |
| 5,403,341 A | | 4/1995 | Solar |
| 5,405,380 A | | 4/1995 | Gianotti et al. |
| 5,409,495 A | * | 4/1995 | Osborn .................... 606/108 |
| 5,415,664 A | | 5/1995 | Pinchuk |
| 5,441,515 A | * | 8/1995 | Khosravi et al. .......... 606/194 |
| 5,445,646 A | * | 8/1995 | Euteneuer et al. ......... 606/198 |
| 5,447,497 A | | 9/1995 | Sogard et al. |
| 5,453,090 A | | 9/1995 | Martinez et al. |
| 5,458,615 A | | 10/1995 | Klemm et al. |
| 5,470,313 A | | 11/1995 | Crocker et al. |
| 5,507,768 A | | 4/1996 | Lau et al. |
| 5,512,051 A | | 4/1996 | Wang et al. |
| 5,534,007 A | | 7/1996 | St. Germain et al. |
| 5,536,252 A | | 7/1996 | Imran et al. |
| 5,571,086 A | * | 11/1996 | Kaplan et al. ............... 604/96 |
| 5,571,089 A | * | 11/1996 | Crocker ...................... 604/96 |
| 5,591,228 A | * | 1/1997 | Edoga ....................... 606/194 |
| 5,632,760 A | * | 5/1997 | Sheiban et al. ............ 606/195 |
| 5,653,691 A | * | 8/1997 | Rupp et al. .................. 604/96 |
| 5,817,102 A | | 10/1998 | Johnson et al. ............ 606/108 |

FOREIGN PATENT DOCUMENTS

| | | |
|---|---|---|
| EP | 0 699 451 A2 | 3/1996 |
| EP | 0 707 837 A1 | 4/1996 |
| WO | WO 93/19703 | 10/1993 |
| WO | WO 96/03072 | 2/1996 |
| WO | WO 96/03092 A1 | 2/1996 |

* cited by examiner

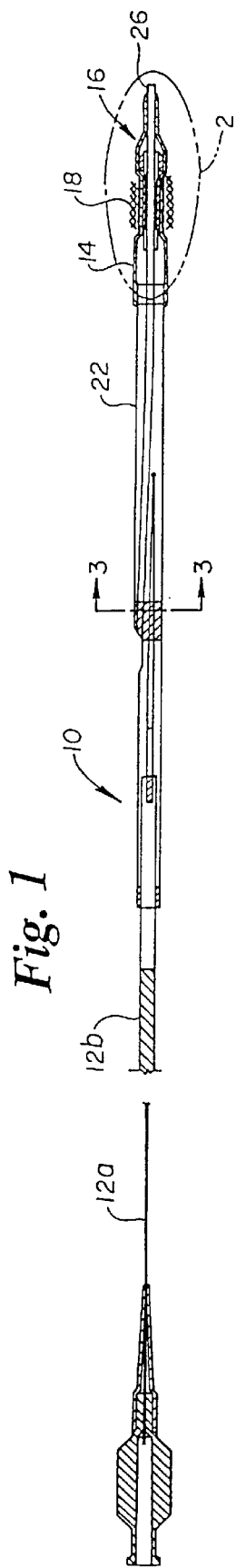
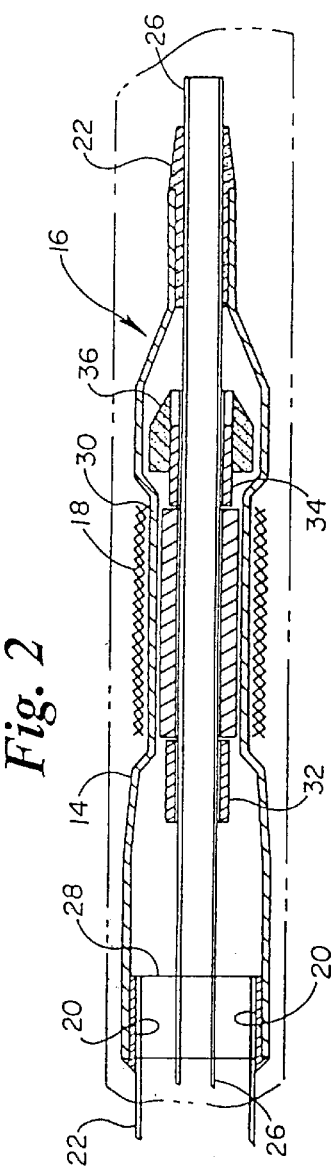

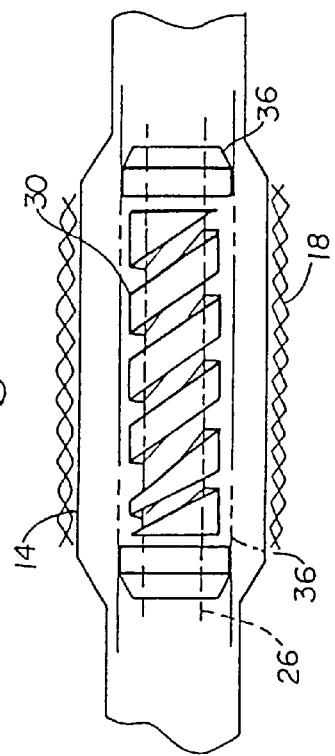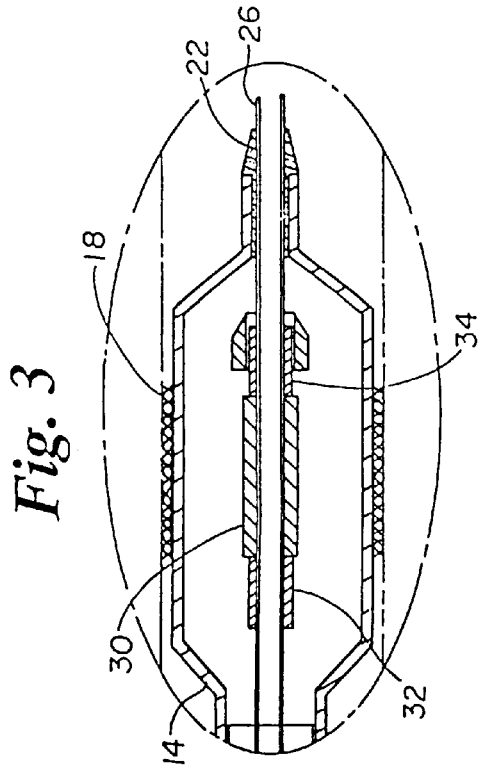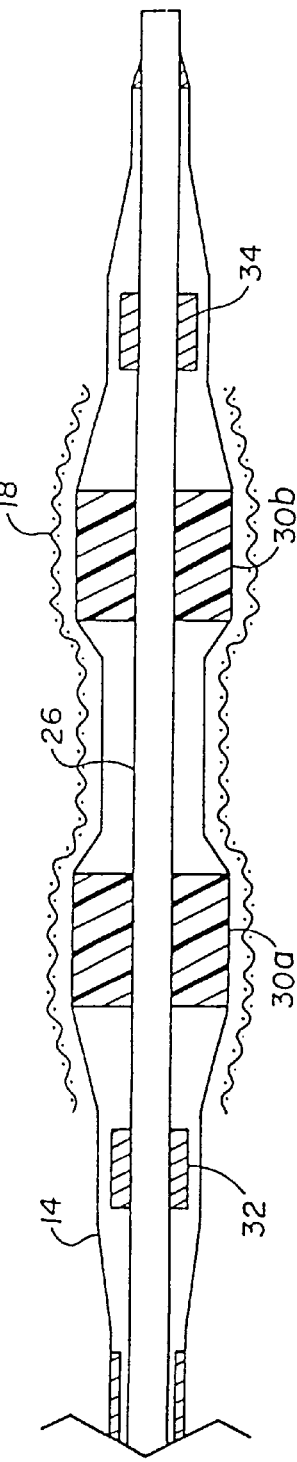

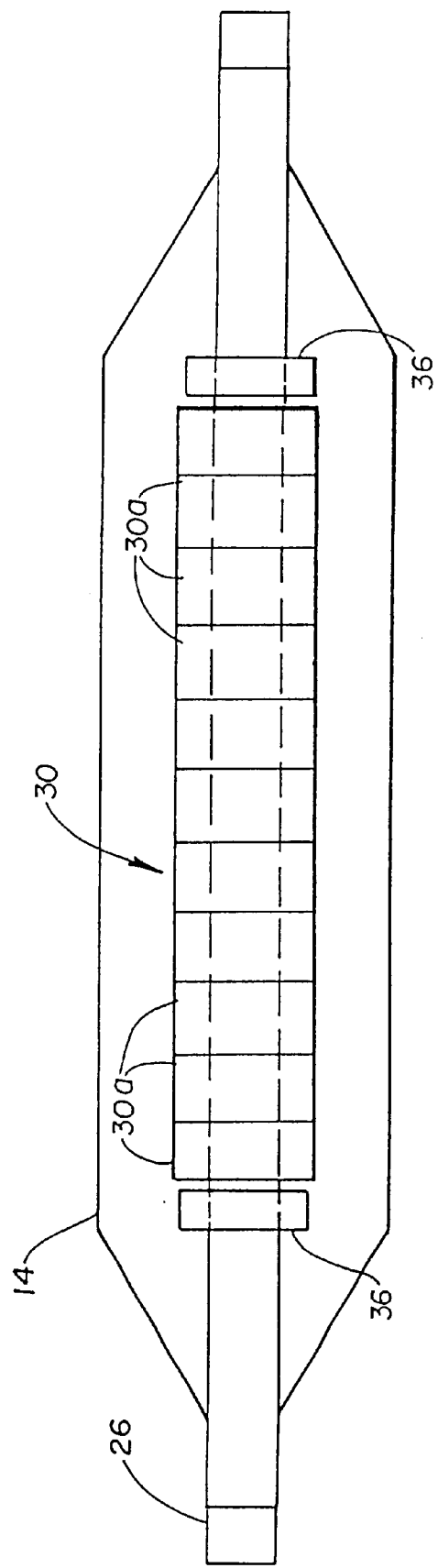

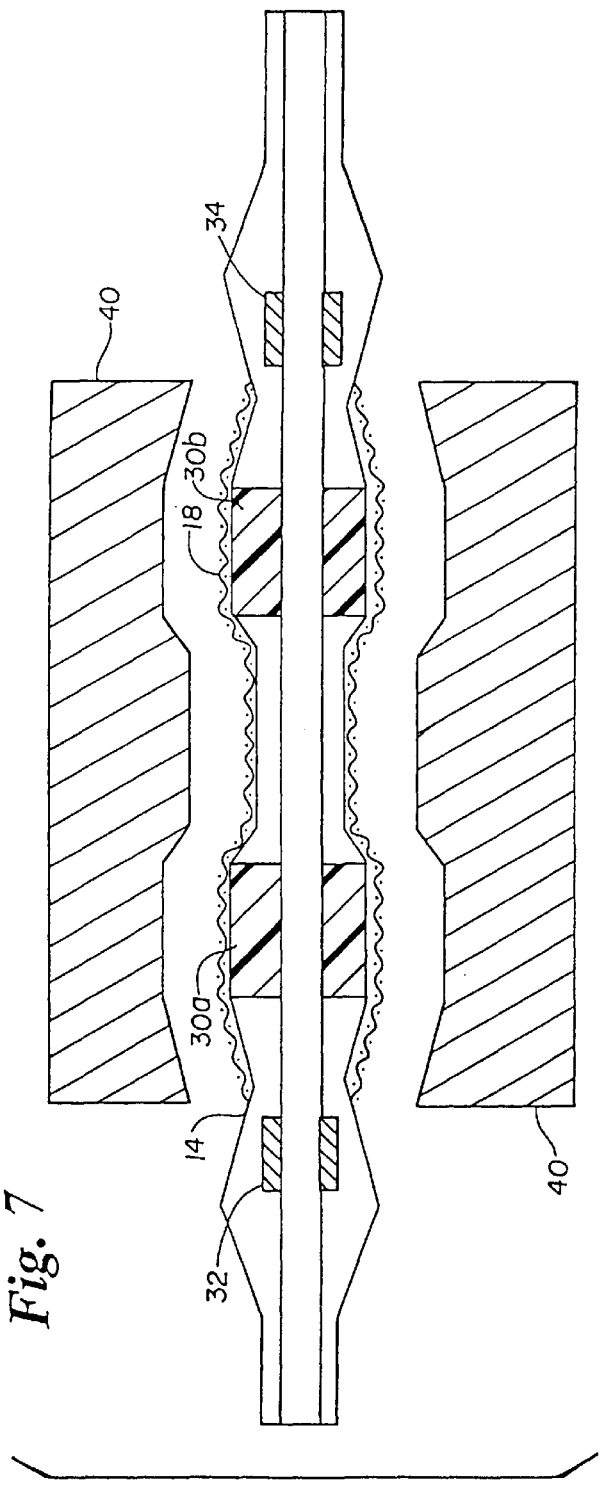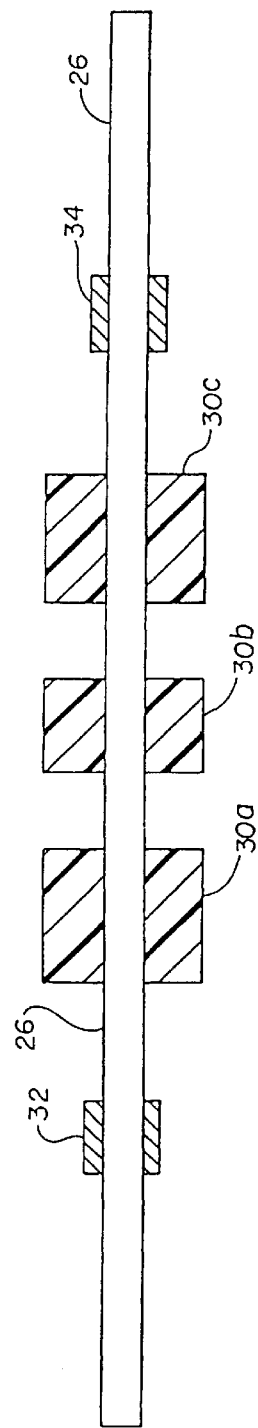

STENT DELIVERY SYSTEM

RELATED APPLICATIONS

The present application a continuation of U.S. application Ser. No. 09/420,249, filed Oct. 19, 1999, now U.S. Pat. No. 6,371,962, which is a continuation of U.S. application Ser. No. 08/702,150, filed on Aug. 23, 1996, now U.S. Pat. No. 6,007,543, which are incorporated herein by reference in their entirety.

BACKGROUND OF THE INVENTION

In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, such as greater than about four atmospheres, to radially compress the arthrosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To prevent restenosis and strengthen the area, a physician can implant an intravascular prosthesis for maintaining vascular patency, called a stent, inside the artery at the lesion. The stent is expanded to a larger diameter for placement in the vasculature, often by the balloon portion of the catheter. Stents delivered to a restricted coronary artery, expanded to a larger diameter as by a balloon catheter, and left in place in the artery at the site of a dilated lesion are shown in U.S. Pat. No. 4,740,207 to Kreamer; U.S. Pat. No. 5,007,926 to Derbyshire; U.S. Pat. No. 4,733,665 to Palmaz; U.S. Pat. No. 5,026,377 to Burton et al.; U.S. Pat. No. 5,158,548 to Lau et al.; U.S. Pat. No. 5,242,399 to Lau et al.; U.S. Pat. No. 5,344,426 to Lau et al.; U.S. Pat. No. 5,415,664 to Pinchuk; U.S. Pat. No. 5,453,090 to Martinez et al.; U.S. Pat. No. 4,950,227 to Savin; U.S. Pat. No. 5,403,341 to Solar; U.S. Pat. No. 5,108,416 to Ryan et al. and European Patent Application No. 707 837 A1 to Sheiban, all of which are incorporated herein by reference. A stent particularly preferred for use with this invention is described in PCT Application No. 960 3092 A1, published Feb. 8, 1996, the content of which is also incorporated herein by reference.

The present invention is particularly directed to improved arrangements for releasably attaching the stent to the catheter to facilitate delivery thereof.

SUMMARY OF THE INVENTION

This invention concerns apparatus suitable for delivery of stents to body cavities. In general, stents are prosthetic devices which can be positioned within a body cavity, for example, a blood vessel of the body of a living human or in some other difficultly accessible place. The stent prosthesis is formed of a generally tubular body, the diameter of which can be decreased or increased. Stents are particularly useful for permanently widening a vessel which is either in a narrowed state, or internally supporting a vessel damaged by an aneurysm. Such stents are typically introduced into the body cavity by use of a catheter. The catheter is usually of the balloon catheter type in which the balloon is utilized to expand the stent, which is positioned over the balloon, to place it in a selected location in the body cavity. The present invention is particularly directed to improved arrangements for releasably attaching the stent to the catheter to facilitate delivery thereof. The stent is held in place on the catheter by means of an enlarged body carried by the catheter shaft within the balloon to which the stent and balloon are fitted, as by crimping.

BRIEF DESCRIPTION OF THE INVENTION

FIG. 1 is an isometric view, a portion of which is enlarged and in longitudinal section, of a balloon catheter having a stent fixed to the catheter by being crimped thereto over the balloon;

FIG. 2 is an even more enlarged view in longitudinal cross-section of the distal end portion of the catheter of FIG. 1;

FIG. 3 is an enlarged cross-sectional view of the distal end portion of the catheter of FIG. 1 similar to that of enlarged view FIG. 2 but showing the balloon in an expanded condition along with the expanded stent;

FIG. 4 is a schematic showing of a preferred mounting body carried by the catheter shaft within the balloon, the body being spirally cut to improve flexibility;

FIG. 5 is a schematic showing in cross-section of another embodiment of the invention with a stent not yet mounted;

FIG. 6 is a schematic showing of another embodiment of the invention;

FIG. 7 is a schematic showing of a means for conveniently crimping the stent on the embodiment shown in FIG. 5, and FIG. 8 is a schematic showing of yet another embodiment of the invention.

DESCRIPTION OF THE PREFERRED EMBODIMENTS

Referring to FIGS. 1–3 a stent delivery system generally indicated at 10 includes a balloon catheter 12 having a balloon 14 on a distal end portion generally indicated at 16. FIG. 1 shows a proximal portion of the catheter at 12*a* and a distal portion 12*b* in enlarged view. FIG. 2 shows the distal end portion 16 in an even more enlarged view. The illustrative catheter 12 is of the type known as a rapid exchange or single operator catheter. However, other types of catheters may be used, such as over the wire and fixed wire types. The balloon 14 is fixed to the catheter 12 by standard means. The balloon is shown in its contracted state in FIGS. 1 and 2. A stent 18 is fixed about the balloon by crimping it thereto. The stent has a larger expanded diameter which is obtained when the balloon is expanded in the known manner. That is, the stent is released from the catheter upon expansion of the balloon as shown in FIG. 3 to be placed in a vessel. When the balloon is then deflated, removal of the balloon and catheter may be accomplished while leaving the stent in place.

As is known in the art the balloon is either bonded at its ends by adhesive 20 and 24, respectively to the outer member 22 of the catheter and to the inner member 26 of the catheter in the manner as shown, or is made one-piece with the outer member as is known in the art. The catheter balloon may be inflated by fluid (gas or liquid) from an inflation port extending from a lumen 28 contained in the catheter shaft and opening into the balloon as shown, or by other known arrangements, depending on the design of the catheter. The details and mechanics of balloon inflation and specific overall catheter construction will vary according to the particular design involved in any given instance, and are known in the art per se. All variations are acceptable for use with this invention.

Any balloon expandable stent may be used with this invention. Many are known in the art including plastic and metal stents. Some are more well known such as the stainless steel stent shown in U.S. Pat. No. 4,735,665; the wire stent shown in U.S. Pat. No. 4,950,227; another metal stent shown in European Patent Application EPO 707 837 A1 and that shown in U.S. Pat. No. 5,445,646. All of these patents are incorporated herein by reference. Also, shape memory metal stents may be used. As already indicated the stent of PCT Application 960 3092 A1 is particularly preferred.

The stent is typically about 16 mm long, while the balloon may be 20 mm long. These dimensions, however, are merely representative for illustrative purposes only and are not meant to be limiting. The stent is positioned over the balloon portion of the dilatation catheter and gently crimped onto the balloon either by hand or with a tool such as a pliers or the like to be mounted for delivery as shown in FIGS. 1 and 2. The crimping may be accomplished by either the manufacturer or the physician.

In accordance with this invention, a mounting body 30, best seen in FIGS. 2 and 3, is included inside balloon 14 to provide a cushion and/or substrate of enlarged diameter relative to the stent shaft to support and hold the stent and secure it during crimping and the delivery procedure. The mounting body may be located only in the body portion of the balloon or may extend into either or both of the cone portions of the balloon.

In the embodiment shown, mounting body 30 is cylindrical in form and takes the shape of a sleeve carried on inner lumen 26, providing an enlarged area or portion for receiving the balloon and stent when the latter is crimped. Marker bands 32 and 34 may also be included on inner 26 as shown. Any radiopaque material such as gold is useful for this purpose. A stop member 36 of generally conical shape or any other shape may also be included on the distal marker band 34 as shown to provide additional resistance to stent movement during delivery and to protect the leading edge of the stent during delivery. A proximal stop member similar to member 36 (not shown) may be optionally included on marker band 32 if desired. Polyethylene or the like is suitable for the stop member(s). Although, the material of the mounting body may be hard, it is preferably of any deformable thermoplastic material, preferably an elastomer material and more preferably of a relatively resilient elastomer material, e.g., lower durometer silicone. A preferred deformable thermoplastic material is high density polyethylene (HDPE). A preferred lower durometer silicone is in the form of tubing. The deformation of resilient material of the mounting body when the stent/balloon is crimped to it causes a radial outward force on the stent/balloon increasing the friction therebetween despite a recoil of the stent.

During delivery, the balloon catheter is advanced through and positioned in a patient's vasculature so that the stent is adjacent to the portion of the vessel where treatment is to take place. The balloon is inflated to expand the stent to an enlarged diameter. When the stent has reached the desired diameter, the balloon is deflated so that the catheter may be removed leaving the stent in place.

Another embodiment of the invention is shown in FIG. 4. In this embodiment the mounting body 30 is a spiral cut elastomer or other suitable material, such as a rigid or flexible plastic, to provide separation for flexibility in that portion of the catheter, allowing more easy movement or tracking around bends. The spiral cut may be only partly through the mounting body or may be all the way through as shown in FIG. 4. Also, while stop members 36 are shown at both ends of mounting body 30 in this embodiment, one, or no stop members may be used.

Another similar version is shown in FIG. 5 which includes a cylindrical mounting body 30 made up of a plurality of separate adjacent rings 30a. Rings 30a may be individual bodies carried on the sheath or bodies cut from a cylinder partially separating them or fully separating them.

The embodiment shown in FIG. 6 includes another feature based on the geometry of the mounting body for further securing the stent upon crimping. This feature is referred to herein as interlocking. That is, the stent may be interlocked to the mount so that the stent cannot slide proximally or distally on the balloon unless it is deformed, such as by expansion. This can be seen by perusing the structure shown in FIG. 6 which includes the inner 26 having a two-piece mounting body made up of spaced mounting bodies 30a and 30b. The spacing between bodies 30a and 30b allows portions of the stent 18 and balloon 14 to be depressed or inserted between the bodies upon crimping of the stent thus forming an interlock against sliding longitudinally before the stent is released.

The interlock formation or crimping is readily accomplished by a two-piece die 40 as shown in FIG. 7 or the like.

FIG. 8 demonstrates that more than a two-piece mounting body arrangement may be used if desired. In this embodiment, the mounting body is comprised of three spaced bodies 30a, 30b and 30c on the inner 26. Preferably in the embodiments of FIGS. 6 and 8, the mounting bodies will be ring-like in shape or cylindrical in shape although other configurations will be readily apparent to those familiar with this art.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A balloon catheter for dilating vascular constrictions and for simultaneously introducing a deformable stent into a vessel to be dilated in order to stabilize the vessel in the dilated condition, wherein a distal region of the catheter, which is intended to receive the deformable stent, comprises: an inner tube that is surrounded and crimped onto by the deformable stent; a balloon arranged between the deformable stent and the inner tube; a pair of longitudinally spaced image sensitive marking sleeves carried on the inner tube within the balloon such that there is a longitudinal space on the inner tube extending between the pair of marking sleeves and such that the deformable stent is substantially centered there-between; an outer tube disposed between the inner tube and the balloon as an intermediate layer, wherein the intermediate layer substantially covers the longitudinal space on the inner tube between the image sensitive marking sleeves, the intermediate layer having an outer diameter, wherein the outer diameter of the intermediate layer is substantially constant between the pair of marking sleeves.

2. A balloon catheter as set forth in claim 1, wherein the inner tube, the balloon, the outer tube forming the intermediate layer and the deformable stent which is crimped onto said catheter form a pre-assembled unit.

3. A balloon catheter as set forth in claim 1, wherein the outer tube comprises an elastic material into which the deformable stent is pressed in the crimping operation.

4. A balloon catheter as set forth in claim 1, wherein the intermediate layer comprises high density polyethylene.

5. A balloon catheter as set forth in claim 1, wherein the intermediate layer includes at least one separation whereby the flexibility of the body and catheter is increased.

6. A balloon catheter as set forth in claim 1, wherein the separation is a spiral separation.

7. A balloon catheter as set forth in claim 5, wherein there are a plurality of separations.

8. A balloon catheter as set forth in claim 7, wherein the plurality of separations are substantially parallel.

9. A balloon catheter as set forth in claim 1, wherein the intermediate layer includes at least one cut in its surface.

10. A balloon catheter as set forth in claim 9, wherein the cut is a spiral separation.

11. A balloon catheter as set forth in claim 9, wherein there are a plurality of cuts.

12. A balloon catheter as set forth in claim 11, wherein the plurality of cuts are circumferential cuts and are substantially parallel.

13. A balloon catheter as set forth in claim 1, further including a stop carried by the inner tube inside the balloon.

14. A balloon catheter as set forth in claim 1, wherein the intermediate layer is generally cylindrical in shape.

15. A balloon catheter as set forth in claim 1, including a pair of stops, each of which is respectively positioned at opposite ends of the deformable stent and carried by the inner tube inside the balloon.

16. Balloon catheter for expansion of vessel stenoses and for simultaneous introduction of a deformable stent, the deformable stent being expandable from an unexpanded condition to an expanded condition, into the vessel which is to be expanded in order to stabilize it in the expanded condition, whereby the distal area of the catheter which is provided for receiving the deformable stent has an interior tube which is surrounded by the unexpanded deformable stent, a balloon is arranged between the deformable stent and the interior tube, and the interior tube has at its ends two sleeves applied to it as image sensitive markers which are composed of material opaque to X rays and are provided within the balloon on the interior tube, the catheter further comprising a intermediate tube which forms an additional plateau and which is composed of a flexible material is provided between interior tube and exterior balloon as an intermediate layer in such manner that it extends in longitudinal direction to the sleeves which form the image sensitive markers, the intermediate layer having an outer diameter, wherein the outer diameter of the intermediate layer is substantially constant between the pair of image sensitive markers.

17. A balloon catheter for introducing a stent, the stent being expandable, into a vessel comprising an inner tube that is surrounded and crimped onto by the stent; a balloon arranged between the stent and the inner tube; a first marking sleeve having a distal end and a proximal end and a second marking sleeve having a distal end, wherein the sleeves are longitudinally spaced from one another along the inner tube, the second marking sleeve being distal to the first marking sleeve along the inner tube, and are image sensitive, the sleeves being carried on the inner tube within the balloon, such that there is a longitudinal space on the inner tube extending between the pair of marking sleeves and such that the stent is substantially centered there-between, an intermediate layer disposed between the inner tube and the balloon, the intermediate layer having a proximal portion and a distal portion, wherein the proximal portion covers the inner tube and is positioned immediately distal to the distal end of the first marking sleeve and wherein the distal portion covers the inner tube and is positioned immediately proximal to the proximal end of the second marking sleeve.

18. The balloon catheter of claim 17, wherein the intermediate layer extends from the distal end of the first marking sleeve to the proximal end of the second marking sleeve.

19. The balloon catheter of claim 17, the first marking sleeve having an outer diameter and the intermediate layer having an inner diameter, wherein the inner diameter of the intermediate layer is equal to or less than the outer diameter of the first marking sleeve.

20. The balloon catheter of claim 18, the intermediate layer having an outer diameter, wherein the outer diameter of the intermediate layer is substantially constant between the pair of marking sleeves.

* * * * *